(12) United States Patent
Mondet

(10) Patent No.: US 6,814,973 B2
(45) Date of Patent: Nov. 9, 2004

(54) COSMETIC USE OF AT LEAST ONE POLYORGANOSILOXANE AS A GELLING AGENT AND COSMETIC COMPOSITION CONTAINING IT

(75) Inventor: Jean Mondet, Aulnay-sous-Bois (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/848,462

(22) Filed: May 4, 2001

(65) Prior Publication Data

US 2001/0051171 A1 Dec. 13, 2001

(30) Foreign Application Priority Data

May 9, 2002 (FR) .............................. 00 05876

(51) Int. Cl.[7] .......................... A61K 7/00; A61K 7/42; A61K 7/021; A61K 7/025; A61K 7/32
(52) U.S. Cl. .......................... 424/401; 424/59; 424/63; 424/54; 424/65; 424/70.1; 424/70.7; 424/70.12; 424/400
(58) Field of Search .................. 424/401, 400, 424/59, 63, 64, 65, 20.1, 70.7, 70.12

(56) References Cited

U.S. PATENT DOCUMENTS

| | | | |
|---|---|---|---|
| 4,744,978 A | | 5/1988 | Homan et al. |
| 5,160,732 A | | 11/1992 | Katsoulis et al. |
| 5,266,321 A | * | 11/1993 | Shukuzaki et al. ......... 424/401 |
| 5,280,019 A | | 1/1994 | Klimisch |
| 5,738,841 A | * | 4/1998 | Mellul et al. ................. 424/59 |
| 5,919,437 A | * | 7/1999 | Lee et al. ..................... 424/68 |
| 6,184,277 B1 | * | 2/2001 | Bara .......................... 524/268 |

FOREIGN PATENT DOCUMENTS

| | | |
|---|---|---|
| DE | 197 07 970 A1 | 9/1998 |
| EP | 0 445 700 A1 | 9/1991 |
| EP | 0 706 790 A1 | 4/1996 |
| EP | 0 751 170 A2 | 1/1997 |
| EP | 0 850 644 A1 | 7/1998 |
| EP | 0 979 643 A2 | 2/2000 |
| FR | 2 708 272 * | 3/1995 |
| FR | 2 765 800 | 1/1999 |
| FR | 2 773 485 | 7/1999 |

OTHER PUBLICATIONS

Abed et al, "Supramolecular association of acid terminated polydimethylsiloxanes", Polymer Bulletin 39, 317–324 (1997); XP–000721177.

* cited by examiner

Primary Examiner—Thurman K. Page
Assistant Examiner—Marina Lamm
(74) Attorney, Agent, or Firm—Nixon & Vanderhye P.C.

(57) ABSTRACT

The present invention relates to the cosmetic use, as a gelling agent, of at least one linear or cyclic polyorganosiloxane which comprises at least two organosiloxy units and at least two side and/or end groups each capable of forming at least one hydrogen bond with one or more partner groups. The invention also relates to a cosmetic composition comprising at least one such polyorganosiloxane in a cosmetically acceptable medium. This cosmetic composition is intended to be used for making up and/or caring for the skin, including the skin of the eyelids, and also for the lips and superficial body growths.

62 Claims, No Drawings

COSMETIC USE OF AT LEAST ONE POLYORGANOSILOXANE AS A GELLING AGENT AND COSMETIC COMPOSITION CONTAINING IT

The present invention relates to the cosmetic use, as a gelling agent, of at least one linear or cyclic polyorganosiloxane which comprises at least two organosiloxy units and at least two side and/or end groups each capable of forming at least one hydrogen bond with one or more partner groups. The invention also relates to a cosmetic composition comprising at least one such polyorganosiloxane in a cosmetically acceptable medium.

In cosmetics, it is desired to obtain compositions which, when applied to the skin, including the skin of the eyelids, and also the lips and superficial body growths, form deposits, for example film-forming deposits, which have one or more desired special cosmetic and/or care effects.

Thus, for make-up compositions such as lipsticks, mascaras and eyeliners, efforts are made to obtain compositions which form deposits with suitable colouring and/or gloss effects. For compositions including an active care agent such as moisturizing products, deodorants and antiperspirants, efforts are made in particular to obtain the optimal effect of the active care agent present in the composition.

In all cases, efforts are also made to obtain the longest possible duration of the cosmetic and/or care effect(s). For example, for lipsticks, mascaras and eyeliners, it is important to obtain sustained staying power of the colouring effect and/or gloss; for foundations, powders, blushers, eyeshadows and body make-up, it is important to obtain a matt effect which is persistent and durable despite friction or the secretion of sebum or sweat; and for compositions including an active care agent, it is important to obtain the longest possible activity of the active agent.

It has been proposed to incorporate silicone oils into cosmetic compositions. The incorporation of these silicone oils into compositions gives deposits properties of hydrophobicity, gloss and a non-greasy feel, but the deposits obtained show poor resistance to external agents such as sweat or sebum, and in particular to mechanical attack such as friction.

Polysiloxanes comprising amide units and possibly comprising groups capable of establishing hydrogen bonds, which are used as gelling agents for silicone oils in cosmetic compositions, are disclosed in patent WO 99/06473 from Colgate-Palmolive. Compositions that are generally solid, transparent or translucent are thus obtained.

U.S. Pat. No. 5,919,441 from Colgate-Palmolive discloses a cosmetic composition based on a fluid component comprising at least one volatile or non-volatile silicone and at least one gelling agent. This gelling agent is a polymer containing both organosiloxy units and groups forming hydrogen bonds which are chosen from ester, urethane, urea, thiourea and amide groups and combinations thereof. The use of such a gelling agent leads, in particular, to solid compositions, that are preferably transparent or translucent.

According to the invention, it has been found that the use of at least one specific polyorganosiloxane, which is different from those disclosed in the patents mentioned above, makes it possible to obtain the gelation of a cosmetically acceptable medium and results in a possible removal of the usual gelling agents.

These specific linear or cyclic polyorganosiloxanes comprise at least two organosiloxy units and at least two side and/or end groups each capable of forming at least one hydrogen bond with one or more partner groups. They have already been disclosed in patent FR 2 708 272 from Rhône-Poulenc as adhesives. However, they have never been used in cosmetics.

The term <<partner group>> means any side and/or end group borne by another molecule of the said polyorganosiloxane, which is capable of forming at least one hydrogen bond with the side and/or end group of the said polyorganosiloxane. This partner group may or may not be identical to the side and/or end group with which it forms at least one hydrogen bond.

The expression <<cosmetically acceptable medium>> means a medium which is compatible with any keratin material such as the skin, the nails, the hair, the eyelashes, the eyebrows, the lips and any other area of body or facial skin, and which also has a pleasant odour, appearance and feel.

One subject of the present invention is thus the cosmetic use as a gelling agent of at least one specific polyorganosiloxane as described below.

Another subject of the present invention is a cosmetic composition comprising, in a cosmetically acceptable medium, at least one specific polyorganosiloxane as described below.

Other characteristics, aspects and advantages of the invention will emerge even more clearly on reading the description and the various examples which follow.

One subject of the invention relates to the use in cosmetics, as a gelling agent, of at least one linear or cyclic polyorganosiloxane which comprises at least two organosiloxy units and at least two side and/or end groups each capable of forming at least one, preferably at least two hydrogen bonds with one or more partner groups.

The polyorganosiloxanes that are suitable in the invention comprise at least two organosiloxy units which may be represented especially by the following formula:

$$R_a R'_b SiO_{(4-a-b)/2} \qquad (I)$$

in which:

R represents a linear, branched or cyclic alkyl group, an aryl group, a polyether group or a fluoro group, R' represents a group capable of forming at least one hydrogen bond, preferably at least two hydrogen bonds, a is 1, 2 or 3, and b is 0 or 1, with the proviso that a+b is equal to 2 or 3.

The number of the said organosiloxy units preferably ranges from 2 to 50,000 and better still from 2 to 30,000.

The alkyl groups may be linear, branched or cyclic, and chosen especially from methyl, ethyl, propyl, isopropyl, n-butyl, sec-butyl, tert-butyl, pentyl, cyclopentyl and cyclohexyl groups and other similar groups. The methyl group is particularly preferred.

Among the aryl groups, the phenyl group is preferred.

Examples of polyether groups which may be mentioned are polyoxyethylene, polyoxypropylene and polyoxyethylene/polyoxypropylene groups.

The fluoro groups may be linear, branched or cyclic alkyl groups, or alkenyl groups, which bear one or more fluorine atoms as substituents.

The groups R' are side and/or end groups capable of forming hydrogen bonds and are preferably chosen from:

(a) groups derived from unprotected or partially protected amino acids, and (b) carboxylic acid, amine or phenol groups of formula:

—X—(Y)$_n$—Z in which:

X represents a linear, branched or cyclic spacer chain, of alkylene or alkenylene type, optionally comprising one or more hetero atoms in the chain, Y represents a monocyclic or polycyclic divalent unsaturated hydrocarbon-based group or a divalent unsaturated heterocyclic group, these polycyclic or heterocyclic groups possibly comprising up to 4 fused rings, n represents an integer ranging from 1 to 4, and Z represents a —COOH or —OH group or a primary, secondary or tertiary amine group, the nitrogen atom of which optionally forms part of a heterocyclic group Y.

As is well known in the art, a carboxylic acid group may form hydrogen bonds with another carboxylic acid group or an amine group, while an amine group may form hydrogen bonds with a carboxylic acid group or a phenolic —OH group.

Thus, it is possible in the composition of the invention to use a single polyorganosiloxane containing at least two end and/or side groups, at least one of which is a —COOH group and at least one other of which is a —COOH or amine (primary, secondary or tertiary) group, or alternatively a single polyorganosiloxane containing at least two end and/or side groups, at least one of which is an amine (primary, secondary or tertiary) group and at least one other of which is a phenolic —OH or —COOH group.

Mixtures, preferably equimolar mixtures, of two polyorganosiloxanes comprising partner groups may also be used. Thus, a mixture of a polyorganosiloxane containing at least two —COOH groups with a polyorganosiloxane containing at least two amine groups, or a mixture of a polyorganosiloxane containing at least two amine groups and of a polyorganosiloxane containing at least two phenolic —OH groups, may be used.

The amine and/or carboxylic acid functions in the groups derived from amino acids may be unprotected or partially protected with specific groups such as the acetyl group. Examples of groups derived from amino acids which may be mentioned include cysteine, N-acetylcysteine, glycocoll, alanine and serine, N-acetylcysteine being particularly preferred.

The functionalization of the polyorganosiloxane with these groups derived from amino acids takes place by techniques that are well known to those skilled in the art, such as the silylation of unsaturated bonds with a thiol derivative of the amino acid or by reacting an organohydrogenosiloxane with an amino acid derivative bearing an unsaturated bond.

The spacer chain X is a linear, branched or cyclic alkylene or alkenylene group which may comprise one or more hetero atoms such as N, S or O. Examples of spacer chains which may be mentioned include —$(CH_2)_p$—S— and —$(CH_2)_p$—O—, p preferably ranging from 1 to 5.

Among the monocyclic or polycyclic divalent unsaturated hydrocarbon-based groups, or unsaturated heterocyclic groups, Y preferably represents a 6-membered aromatic nucleus which may comprise one or more hetero atoms.

Monocyclic or polycyclic divalent unsaturated hydrocarbon-based groups which may be mentioned include phenylene or naphthalene-diyl groups, the phenylene group being particularly preferred.

When Y represents an unsaturated heterocyclic group containing a nitrogen atom, for example, Z may represent an amine group whose nitrogen atom forms part of the heterocyclic group Y and Y—Z is chosen especially from pyridyl, pyrimidinyl and diazanaphthalene-diyl groups.

The polyorganosiloxanes that are suitable in the present invention are linear or cyclic polyorganosiloxanes comprising at least two organosiloxy units and at least two side and/or end groups capable of forming hydrogen bonds, such as those disclosed in the document FR 2 708 272 mentioned above.

The polyorganosiloxane which is preferred in the present invention corresponds to the following formula:

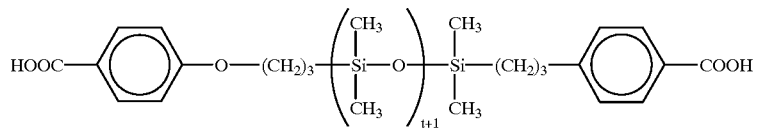

with t preferably ranging from 1 to 1200 and in particular with t=11.

Another subject of the invention relates to a cosmetic composition comprising, in a cosmetically acceptable medium, at least one linear or cyclic polyorganosiloxane which comprises at least two organosiloxy units and at least two side and/or end groups each capable of forming at least one hydrogen bond with one or more partner groups, the said organosiloxy units being represented by the following formula:

in which R, R', a and b are as defined above.

The preparation of the polyorganosiloxanes in the compositions of the invention is known in the art. Preparation examples are disclosed in French patent No. 2 708 272 from Rhône-Poulenc and in the article by S. Abed et al., *Polym. Mater. Sci. Ena.*, 1997, No. 76, 45–46.

A first preparation example consists in using a polyorganosiloxane containing unsaturated side groups, such as vinyl or allylic groups, and in reacting it with a sulphanilic derivative such as N-acetylcysteine. A polyorganosiloxane comprising the following units:

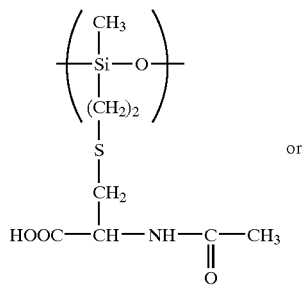

or

-continued

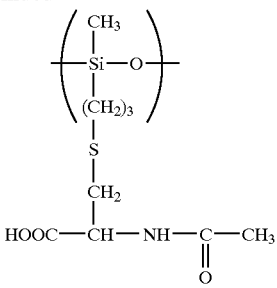

may thus be obtained.

A second preparation example consists in using a polyorganosiloxane containing silyl groups —SiH and in reacting it by hydrosilylation with an amino acid derivative bearing a vinyl or allylic double bond, the carboxylic acid and amine functions of which have been neutralized by silylation, such as, for example:

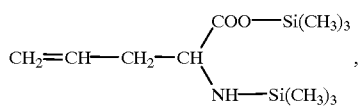

and then, once the hydrosilylation reaction is complete, in deprotecting the carboxylic acid and amine functions. Units of the same type as those represented above are thus obtained.

The synthesis of polyorganosiloxanes containing p-carboxyphenyloxy end groups is disclosed in the article by S. Abed et al., *Polym. Bull.*, 39, 1997, pages 317–324. It consists in first preparing a benzyl p-allyloxybenzoate and in reacting it with a polyorganosiloxane containing —SiH end groups by hydrosilylation. The final step consists in deprotecting the end groups to finally obtain the following product:

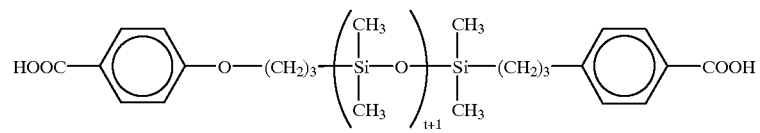

with t preferably ranging from 1 to 1200.

In the cosmetic composition of the invention, the polyorganosiloxane corresponding to the above formula with t=11 is preferably used.

The polyorganosiloxanes of the present invention are used in particular in an amount which is within the range from 0.5% to 50% by weight and preferably from 1% to 30% by weight relative to the total weight of the cosmetic composition.

The cosmetically acceptable medium may comprise a fatty phase, optionally organic solvents and optionally water in an amount such that it does not interfere with the groups of the polyorganosiloxane for the formation of hydrogen bonds.

The fatty phase consists in particular of fatty substances that are liquid at room temperature (generally 25° C.) and/or of fatty substances that are solid at room temperature, such as waxes, gums and pasty fatty substances, and mixtures thereof.

As fatty substances that are liquid at room temperature, often referred to as oils, which may be used in the invention, mention may be made of silicone oils, hydrocarbon-based oils, of mineral, animal, plant or synthetic origin, alone or as a mixture provided that they form a homogeneous and stable mixture and provided that they are compatible with the intended use.

The cosmetically acceptable medium preferably contains volatile and/or non-volatile silicone oils.

Non-volatile silicone oils which may be mentioned are polydimethylsiloxanes (PDMSs), that are optionally phenylated, such as phenyltrimethicones, phenyltrimethylsiloxydiphenylsiloxanes, diphenylmethyldimethyltrisiloxanes, diphenyldimethicones, phenyldimethicones and polymethylphenylsiloxanes, optionally substituted with aliphatic and/or aromatic groups, or optionally fluorinated; polysiloxanes modified with fatty acids, fatty alcohols or polyoxyalkylenes, fluorosilicones and perfluorosilicone oils, and mixtures thereof.

Among the non-volatile silicone oils that are preferred, mention may be made of polydimethylsiloxanes, polymethylphenylsiloxanes, silicones comprising polyoxyalkylene blocks or grafts, in particular polyoxyethylene or copoly(oxyethylene/oxypropylene) blocks or grafts, such as dimethicone copolyols, silicones bearing both hydrophobic hydrocarbon-based groups (for example $C_2$–$C_{30}$ alkyl groups) and polyoxyethylenated or copoly(oxyethylenated/oxypropylenated) blocks or grafts, such as alkyldimethicone copolyols, silicones bearing fluoro or perfluoro groups such as perfluoroalkyl polydimethylsiloxanes and perfluoroalkyl polymethylphenylsiloxanes, and mixtures thereof.

One or more oils that are volatile at room temperature may also be used advantageously. After evaporating off these oils, a supple film-forming deposit is obtained. These volatile oils also make it easier to apply the composition to the skin, the lips and superficial body growths.

The term <<volatile oil>> means an oil which is capable of evaporating at the temperature of the skin or the lips, and which has a non-zero vapour pressure at room temperature and under atmospheric pressure, ranging in particular from 0.13 to $4.0 \times 10^4$ Pa ($10^{-3}$ to 300 mm Hg) and better still greater than 40 Pa (0.3 mm Hg).

These oils may be silicone oils optionally comprising alkyl or alkoxy groups at the end of or pendent on a silicone chain.

As volatile silicone oils which may be used in the invention, mention may be made of linear or cyclic silicones with a viscosity at room temperature and under atmospheric pressure of less than 8 $mm^2/s$ (8 cSt) and in particular comprising from 2 to 7 silicon atoms. Mention may be made in particular of octamethylcyclotetrasiloxane, decamethylcyclopentasiloxane, hexadecamethylcyclohexasiloxane, heptamethylhexyltrisiloxane and heptamethyloctyltrisiloxane, and mixtures thereof.

Preferably, at least one volatile silicone oil chosen especially from octamethylcyclotetrasiloxane, decamethylcyclopentasiloxane, hexadecamethylcyclohexasiloxane, heptamethylhexyltrisiloxane, heptamethyloctyltrisiloxane, octamethyltrisiloxane and decamethyltetrasiloxane, and mixtures thereof, may be used.

The cosmetically acceptable medium containing one or more silicone oils may also contain one or more oils of non-silicone nature such as, for example, hydrocarbon-based oils.

The term <<hydrocarbon-based oil>> means an oil predominantly containing carbon and hydrogen atoms, and in particular alkyl or alkenyl chains such as alkanes or alkenes, as well as an oil not only containing hydrogen and carbon atoms, but also oxygen atoms, in the form of an ether, ester, alcohol or carboxylic acid function.

Mention may also be made of hydrocarbon-based oils such as liquid paraffin or liquid petroleum jelly, mink oil, turtle oil, soyabean oil, perhydrosqualene, sweet almond oil, beauty-leaf oil, palm oil, grape pip oil, sesame oil, corn oil, parleam oil, arara oil, rapeseed oil, sunflower oil, cottonseed oil, apricot oil, castor oil, avocado oil, jojoba oil, olive oil or cereal germ oil; esters of linoleic acid, of oleic acid, of lauric acid or of stearic acid; fatty esters, such as isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate or lactate, bis(2-ethylhexyl) succinate, diisostearyl malate and glyceryl or diglyceryl triisostearate; higher fatty alcohols containing at least 12 carbon atoms, such as stearyl alcohol, oleyl alcohol, linoleyl alcohol, linolenyl alcohol, isostearyl alcohol or octyldodecanol.

For the purposes of the present invention, a wax is a lipophilic compound which is solid at room temperature (about 25° C.), which undergoes a reversible solid/liquid change of state, which has a melting point above about 40° C. which may be up to 200° C., and which has an anisotropic crystal organization in the solid state. In general, the size of the wax crystals is such that the crystals scatter and/or diffuse light, giving the composition comprising them a more or less opaque cloudy appearance. By bringing the wax to its melting point, it is possible to make it miscible with oils and to form a microscopically homogeneous mixture, but on returning the temperature of the mixture to room temperature, a recrystallization of the wax in the oils of the mixture is obtained, which may be detected microscopically and macroscopically (opalescence).

As examples of waxes which may be used according to the invention, mention may be made of waxes of animal origin such as beeswax, spermaceti, lanolin wax and lanolin derivatives; plant waxes such as carnauba wax, candelilla wax, ouricury wax, Japan wax, cocoa butter, cork fibre wax of sugar cane wax; mineral waxes, for example paraffin wax, petroleum jelly wax, lignite wax, microcrystalline waxes or ozokerites; synthetic waxes including polyethylene wax, polytetrafluoroethylene wax and the waxes obtained by Fisher-Tropsch synthesis, or alternatively silicone waxes, hydrogenated oils that are solid at 25° C., such as hydrogenated castor oil, hydrogenated jojoba oil, hydrogenated palm oil, hydrogenated tallow and hydrogenated coconut oil, and fatty esters that are solid at 25° C., such as the $C_{20}$–$C_{40}$ alkyl stearate sold under the trade name <<Kester Wax K82H>> by the company Koster Keunen.

The gums are generally high molecular weight polydimethylsiloxanes (PDMSs) and the pasty substances are generally hydrocarbon-based compounds, for instance lanolins and derivatives thereof, or PDMSs.

The cosmetic composition according to the invention may also comprise one or more cosmetically acceptable (acceptable tolerance, toxicology and feel) organic solvents. These organic solvents may be chosen from hydrophilic organic solvents, lipophilic organic solvents and amphiphilic solvents, and mixtures thereof.

Among the hydrophilic organic solvents which may be mentioned, for example, are linear or branched lower monoalcohols containing from 1 to 8 carbon atoms, for instance ethanol, propanol, butanol, isopropanol, isobutanol; acetone; polyethylene glycols containing from 6 to 80 ethylenoxy units; polyols such as propylene glycol, butylene glycol, glycerol or sorbitol; mono- or dialkyl isosorbides in which the alkyl groups contain from 1 to 5 carbon atoms, for instance dimethyl isosorbide; for instance diethylene glycol monomethyl ether or monoethyl ether and propylene glycol ethers such as dipropylene glycol methyl ether.

Amphiphilic organic solvents which may be mentioned include polyols such as polypropylene glycol (PPG) derivatives, for instance polypropylene glycol esters of fatty acids, and PPG ethers of fatty alcohols, for example PPG-36 oleate and PPG-23 oleyl ether.

Lipophilic organic solvents which may be mentioned, for example, include hydrocarbons such as hexane, heptane and octane; fatty esters such as diisopropyl adipate and dioctyl adipate; alkyl benzoates; dioctyl malate.

The cosmetic composition according to the invention may also comprise at least one ingredient chosen from cosmetic active agents and/or active care agents depending on the type of application envisaged, and also various other conventional additives used in cosmetics, such as, for example, fillers, pigments, colourants, surfactants, sunscreens, antioxidants, fragrances or preserving agents.

The cosmetic active agents and/or active care agents are used in a proportion that is usual to those skilled in the art, and in particular in a proportion ranging from 0.001% to 30% by weight of the composition.

A person skilled in the art will take care to select the optional additives and the amount thereof such that they do not harm the properties of the cosmetic compositions, that is to say they should not have functional groups capable of forming hydrogen bonds with the main components of the cosmetic composition, which have been described above.

The fillers may be mineral or organic, and lamellar or spherical. Mention may be made of talc, mica, silica, kaolin, Nylon® (Orgasol® from Atochem) powder, poly-__-alanine powder and polyethylene powder, Teflon®, lauroyllysine, starch, boron nitride, hollow microspheres such as Expancel® (Nobel Industry), Polytrap® (Dow Corning) and silicone resin microbeads (Tospearls® from Toshiba, for example), precipitated calcium carbonate, magnesium carbonate and magnesium hydrocarbonate, hydroxyapatite, hollow silica microspheres (silica beads from Maprecos), glass or ceramic microcapsules, metal soaps derived from organic carboxylic acids containing from 8 to 22 carbon atoms and preferably from 12 to 18 carbon atoms, for example zinc, magnesium or lithium stearate, zinc laurate or magnesium myristate.

The pigments may be white or coloured, and mineral and/or organic. Among the mineral pigments which may be mentioned are titanium dioxide, optionally surface-treated, zirconium oxide or cerium oxide, and iron oxide or chromium oxide, manganese violet, ultramarine blue, chromium hydrate and ferric blue. Among the organic pigments which may be mentioned are carbon black, pigments of D&C type, and lakes based on cochineal carmine or on barium, strontium, calcium or aluminium.

The nacreous pigments may be chosen from white nacreous pigments such as mica coated with titanium oxide or with bismuth oxychloride, coloured nacreous pigments such as titanium mica with iron oxides, titanium mica with, in particular, ferric blue or chromium oxide, titanium mica with an organic pigment of the abovementioned type and nacreous pigments based on bismuth oxychloride.

The liposoluble colorants are, for example, Sudan Red, DC Red 17, DC Green 6, __-carotene, DC Yellow 11 or DC Violet 2. They may represent from 0.01% to 20% of the weight of the composition and better still from 0.1% to 6%.

The surfactants may be anionic, cationic or nonionic surfactants.

The sunscreens are chosen from sunscreens that are active in the UV-A and UV-B range.

In one particular embodiment of the invention, the cosmetic compositions may be prepared in the usual manner by a person skilled in the art and may be in the form of a cast product, for example in the form of a stick or tube, or in the form of a dish which may be used by direct contact or with the aid of a sponge. In particular, they find an application for make-up and/or care of the skin, the lips and superficial body growths, as cast foundations, cast blushers or eyeshadows, lipsticks, lipcare bases or balms, concealer products, deodorants, antiperspirants, make-up products for the body such as semi-permanent tattoos, antisun products or mascara blocks. They may also be in the form of a soft paste, with a dynamic viscosity at 25° C. of about from 1 to 40 Pa·s, as measured using a Haake RS 50 machine, with a viscosity extrapolated to shear rates of less than 1 s$^{-1}$. They may also be in the form of a thickened solution whose viscosity is at least twice that of the base oil(s) containing no gelling agent.

The compositions are advantageously anhydrous and may contain up to 5% water relative to the total weight of the composition. In this case, they may be in particular in the form of an oily gel, oily liquid or oil, paste or stick. These various forms are prepared according to the usual methods of the fields under consideration.

The examples which follow illustrate the present invention.

Synthesis of Compound A

A polyorganosiloxane containing p-carboxyphenyloxy end groups as defined above is prepared according to the process described in the article by S. ABED, Polymer Bulletin, 39, 317–324 (1997). Compound A of the formula below is thus obtained:

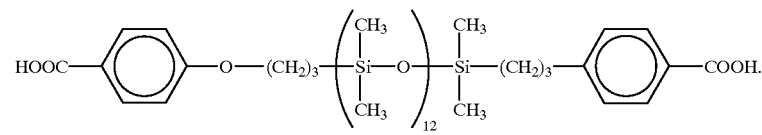

This compound A is used in the examples which follow for the preparation of lipstick and lip gloss.

EXAMPLE 1

A lipstick is prepared having the following composition:

| | |
|---|---|
| Performalene 500 ®[(1)] polyethylene wax | 15 g |
| Compound A | 5 g |
| Pigments | 9 g |
| Hydrogenated polyisobutylene oil[(2)] | 35.5 g |
| Dow 556 Fluid ®[(3)] phenyltrimethicone oil | 35.5 g |

[(1)]sold by the company Petrolite
[(2)]of viscosity 34 mm$^2$/s (34 cSt) at 25° C., sold under the name <<Parleam ®>> by the company Nippon Oil-Fats.
[(3)]sold by the company Dow Corning.

The constituents of the above composition are all mixed together at 110° C. After homogenizing and grinding the pigments, the mixture is cast in a suitable mould. A stick which has good Theological properties is thus obtained. It deposits on the lips a film which has good staying power over time.

EXAMPLE 2

A lip gloss having the composition below is prepared:

| | |
|---|---|
| Compound A | 5 g |
| Pigment (DC Red No. 7 Calcium (lake)) | 5 g |
| Dow 556 Fluid ®(*) phenyltrimethicone oil | 90 g |

(*)sold by the company Dow Corning.

Compound A is first dissolved in the oil. A lip gloss is obtained by dispersing the pigments in this fatty phase. The lip gloss thus obtained may be applied to the lips with a brush. It gives a long-lasting, glossy colouring effect.

EXAMPLE 3

An anhydrous antisun product having the composition below is prepared:

| | |
|---|---|
| Compound A | 5 g |
| Nanometric TiO$_2$ coated with alumina and aluminium stearate(*). | 7 g |
| Phenyltrimethicone oil Dow 556 Fluid ®(**) qs | 100 g |

(*)sold under the name MT 100T by the company Tayca
(**)sold by the company Dow Corning.

Compound A is first dissolved in the oil. An antisun product is obtained by dispersing the pigment by grinding in the medium. The antisun product has water-resistance and sebum-resistance properties.

What is claimed is:

1. A method of gelling a cosmetic composition comprising adding to a cosmetic composition, as a gelling agent, at least one linear or cyclic polyorganosiloxane which comprises at least two organosiloxy units and at least two side groups or end groups, each of said groups being capable of forming at least one hydrogen bond with one or more partner groups, the said organosiloxy units being represented by the following formula:

$$R_aR'_bSiO_{(4-a-b)/2}$$

in which:
R represents a linear, branched or cyclic alkyl group, an aryl group, a polyether group or a fluoro group,
R' represents a group capable of forming at least one hydrogen bond,
a is 1, 2 or 3, and
b is 0 or 1, with the proviso that a+b is equal to 2 or 3, the said group R' being selected from the group consisting of:
(a) a group derived from unprotected or partially protected amino acid, and
(b) a carboxylic acid, an amine or a phenol group of formula:

—X—(Y)$_n$—Z in which:

X represents a linear, branched or cyclic alkylene or alkenylene spacer chain, optionally comprising one or more hetero atoms in the chain, Y represents a monocyclic or polycyclic divalent unsaturated hydrocarbon-based group, said polycyclic group optionally comprising up to 4 fused rings, n represents an integer ranging from 1 to 4, and Z represents a —COOH or —OH group or a primary, secondary or tertiary amine group.

2. A method according to claim 1, wherein the polyorganosiloxane contains from 2 to 50,000 organosiloxy units.

3. A method according to claim 1, wherein the side groups or end groups of the polyorganosiloxane are each capable of forming at least two hydrogen bonds with one or more partner groups.

4. A method according to claim 1, wherein Y represents a 6-membered aromatic nucleus and Z represents a —COOH group.

5. A method according to claim 4, wherein the polyorganosiloxane corresponds to the following formula:

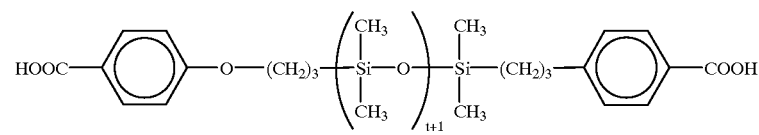

with t ranging from 1 to 1200.

6. A method according to claim 5, wherein the polyorganosiloxane corresponds to the following formula:

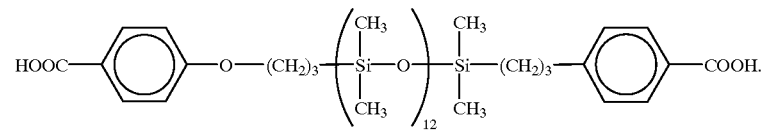

7. Cosmetic composition comprising in a cosmetically acceptable medium comprising a fatty phase, at least one linear or cyclic polyorganosiloxane, which comprises at least two organosiloxy units and at least two side groups or end groups which are capable of forming at least one hydrogen bond with one or more partner groups, the said organosiloxy units being represented by the following formula:

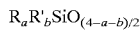

in which:
R represents a linear, branched or cyclic alkyl group, an aryl group, a polyether group or a fluoro group,
R' represents a group capable of forming at least one hydrogen bond,
a is 1, 2, or 3 and
b is 0 or 1, with the proviso that a+b is equal to 2 or 3, the said group R' being selected from the group consisting of:
(a) a group derived from an unprotected or a partially protected amino acid, and
(b) a carboxylic acid, an amine or a phenol group or formula:

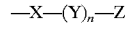

in which:
X represents a linear, branched or cyclic alkylene or alkenylene spacer chain; optionally comprising one or more hetero atoms in the chain,
Y represents a monocyclic or polycyclic divalent unsaturated hydrocarbon-based group, said polycyclic group optionally comprising up to 4 fused rings,
n represents an integer ranging from 1 to 4, and Z represents a —COOH or —OH group or a primary, a secondary, or tertiary amine group.

8. Cosmetic composition according to claim 7, wherein the polyorganosiloxane is between 2 and 50,000 organosiloxane units.

9. Cosmetic composition according to claim 7, wherein the side groups or end groups of the polyorganosiloxane are each capable of forming at least two hydrogen bonds with one or more partner groups.

10. Cosmetic composition according to claim 7, wherein Y represents a 6-membered aromatic nucleus and Z represents a —COOH group.

11. Cosmetic composition according to claim 10, wherein the polyorganosiloxane corresponds to the following formula:

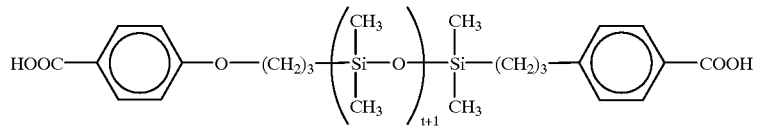

with t ranging from 1 to 1200.

12. Cosmetic composition according to claim 11, wherein the polyorganosiloxane corresponds to the following formula:

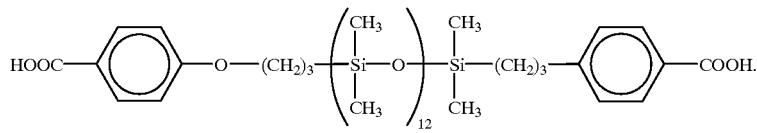

13. Cosmetic composition according to claim 7, wherein the amount of the polyorganosiloxane is between 0.5% and 50% by weight relative to the total weight of the cosmetic composition.

14. Cosmetic composition according to claim 13, wherein the amount of the polyorganosiloxane is between 1% and 30% by weight relative to the total weight of the cosmetic composition.

15. Cosmetic composition according to claim 7, wherein the fatty phase comprises fatty substances that are liquid at room temperature and/or fatty substances that are solid at room temperature.

16. Cosmetic composition according to claim 15, wherein the fatty substances that are liquid at room temperature comprise at least one of a silicone oil and a hydrocarbon-based oil.

17. Cosmetic composition according to claim 16, comprising at least one silicone oil.

18. Cosmetic composition according to claim 17, wherein the silicons oil is selected from the group consisting of polydimethylsiloxanes (PDMSs), which are optionally phenylated; polymethylphenylsiloxanes, which are substituted with aliphatic and/or aromatic groups, or optionally fluorinated; polysiloxanes modified with fatty acids, fatty alcohols or polyoxyalkylenes; fluorosilicones and perfluorosilicone oils.

19. Cosmetic composition according to claim 16, wherein the hydrocarbon-based oil is selected from the group consisting of liquid paraffin, liquid petroleum jelly, mink oil, turtle oil, soybean oil, perhydrosqualene, sweet almond oil, beauty-leaf oil, palm oil, grape pip oil, sesame oil, corn oil, parleam oil, arara oil, rapeseed oil, sunflower oil, cottonseed oil, apricot oil, castor oil, avocado oil, jojoba oil, olive oil, cereal germ oil; an ester of linoleic acid, an ester of oleic acid, an ester of lauric acid, an ester of stearic acid a fatty ester, and a higher fatty alcohols containing at least 12 carbon atoms.

20. Cosmetic composition according to claim 15, wherein the fatty substances that are solid at room temperature comprise waxes, gums and/or pasty fatty substances.

21. Cosmetic composition according to claim 20, wherein the waxes are selected from the group consisting of waxes of animal origin, plant waxes, mineral waxes, synthetic waxes, waxes obtained by Fisher-Tropsch synthesis, silicone waxes and hydrogenated oils that are solid at 25° C.

22. Cosmetic composition according to claim 20, wherein the gums are selected from the group consisting of high molecular weight polydimethylsiloxanes.

23. Cosmetic composition according to claim 20, wherein the pasty fatty substances are selected from the group consisting of hydrocarbon-based compounds and polydimethylsiloxanes.

24. Cosmetic composition according to claim 7, further comprising at least one additive selected from the group consisting of a filler, a pigment, a colorant, a surfactant, a sunscreen, an antioxidant, a fragrance and a preserving agent.

25. Cosmetic composition according to claim 7, wherein said composition is anhydrous.

26. Cosmetic composition according to claim 7, wherein said composition is in the form of a stick, a tube, a soft paste, with a dynamic viscosity at 25° C. of about from 1 to 40 Pa.s, a dish, an oily gel or an oily liquid.

27. A method of making up and/or caring for the skin, comprising a composition of claim 7, to said skin.

28. Cosmetic composition according to claim 7, in the form of a lipstick, a mascara, an eyeliner, a foundation, a powder, a blusher, an eyeshadow or a body make-up.

29. Cosmetic composition according to claim 7, in the form of a moisturizing product, a deodorant or an antiperspirant.

30. A method according to claim 2, wherein the polyorganosiloxane contains from 2 to 30,000 organosiloxy units.

31. A cosmetic composition according to claim 8, wherein the polyorganosiloxane contains from 2 to 30,000 organosiloxy units.

32. A cosmetic composition of claim 18, wherein the silicone oil is selected from the group consisting of a phenyltrimethicone, a phenyltrimethylsiloxy-diphenylsiloxane, a diphenylmethyldimethyltrisiloxane, a diphenyldimethicone, and a phenyldimethicone.

33. A cosmetic composition according to claim 19, wherein said oil is selected from the group consisting of isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate or lactate, bis(2-ethylhexyl) succinate, dilsostearyl malate, glyceryl trilsostearate, diglyceryl trilsostearate, stearyl alcohol, oleyl alcohol, linoleyl alcohol, linolenyl alcohol, isostearyl alcohol and octyldodecanol.

34. A method of claim 27, wherein said skin is selected from the group consisting of eyelids, lips and nails.

35. Cosmetic composition comprising, in a cosmetically acceptable medium, at least one linear or cyclic polyorganosiloxane, which comprises at least two organosiloxy units and at least two side groups or end groups which are each capable of forming at least one hydrogen bond with one or more partner groups, the said organosiloxy units being represented by the following formula:

$$R_a R'_b SiO_{(4-a-b)/2}$$

in which:
R represents a linear, branched or cyclic alkyl group, an aryl group, a polyether group or a fluoro group,
R' represents a group capable of forming at least one hydrogen bond,
a is 1, 2 or 3, and
b is 0 or 1, with the proviso that a+b is equal to 2 or 3, the said group R' is a carboxylic acid, an amine or a phenol group of formula:

—X—(Y)$_n$—Z in which:
X represents a linear, branched or cyclic alkylene or alkenylene spacer chain, optionally comprising one or more hetero atoms in the chain, Y represents a monocyclic or polycyclic divalent unsaturated hydrocarbon-based group, said polycyclic group optionally comprising up to 4 fused rings, n represents an integer ranging from 1 to 4, and Z represents a —COOH or —OH group or a primary, secondary or tertiary amine group.

36. Cosmetic composition according to claim 35, wherein the polyorganosiloxane comprises from 2 to 50,000 organosiloxy units.

37. Cosmetic composition according to claim 35, wherein the side groups or end groups of the polyorganosiloxane are each capable of forming at least two hydrogen bonds with one or more partner groups.

38. Cosmetic composition according to claim 35, wherein Y represents a 6-membered aromatic nucleus and Z represents a —COOH group.

39. Cosmetic composition according to claim 38, wherein the polyorganosiloxane corresponds to the following formula:

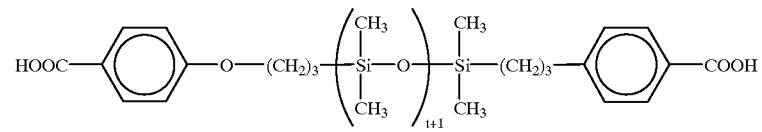

with t ranging from 1 to 1200.

40. Cosmetic composition according to claim 39, wherein the polyorganosiloxane corresponds to the following formula:

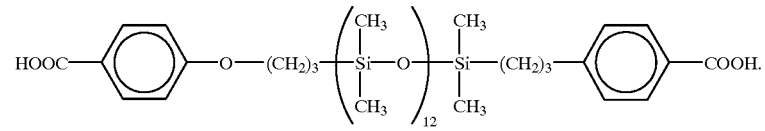

41. Cosmetic composition according to claim 35, wherein the amount of the polyorganosiloxane is between 0.5% and 50% by weight relative to the total weight of the cosmetic composition.

42. Cosmetic composition according to claim 41, wherein the amount of the polyorganosiloxane is between 1% and 30% by weight relative to the total weight of the cosmetic composition.

43. Cosmetic composition according to claim 35, wherein the cosmetically acceptable medium comprises a fatty phase, optionally organic solvents and optionally water.

44. Cosmetic composition according to claim 43, wherein the fatty phase comprises fatty substances that are liquid at room temperature and/or fatty substances that are solid at room temperature.

45. Cosmetic composition according to claim 44, wherein the fatty substances that are liquid at room temperature comprise at least one of a silicone oil and a hydrocarbon-based oil.

46. Cosmetic composition according to claim 45, comprising at least one silicone oil.

47. Cosmetic composition according to claim 46, wherein the silicone oil is selected from the group consisting of polydimethylsiloxanes (PDMSs), which are optionally phenylated; polymethylphenylsiloxanes, which are substituted with aliphatic and/or aromatic groups, or optionally fluorinated; polysiloxanes modified with fatty acids, fatty alcohols or polyoxyalkylenes; fluorosilicones and perfluorosilicone oils.

48. Cosmetic composition according to claim 45, wherein the hydrocarbon-based oil is selected from the group consisting of liquid paraffin, liquid petroleum jelly, mink oil, turtle oil, soybean oil, perhydrosqualene, sweet almond oil, beauty-leaf oil, palm oil, grape pip oil, sesame oil, corn oil, parleam oil, arara oil, rapeseed oil, sunflower oil, cottonseed oil, apricot oil, castor oil, avocado oil, jojoba oil, olive oil, cereal germ oil; an ester of linoleic acid, an ester of oleic acid, an ester of lauric acid, an ester of stearic acid a fatty ester, and a higher fatty alcohols containing at least 12 carbon atoms.

49. Cosmetic composition according to claim 44, wherein the fatty substances that are solid at room temperature comprise waxes, gums and/or pasty fatty substances.

50. Cosmetic composition according to claim 49, wherein the waxes are selected from the group consisting of waxes of animal origin, plant waxes, mineral waxes, synthetic waxes, waxes obtained by Fisher-Tropsch synthesis, silicone waxes and hydrogenated oils that are solid at 25° C.

51. Cosmetic composition according to claim 49, wherein the gums are selected from the group consisting of high molecular weight polydimethylsiloxanes.

52. Cosmetic composition according to claim 49, wherein the pasty fatty substances are selected from the group consisting of hydrocarbon-based compounds and polydimethylsiloxanes.

53. Cosmetic composition according to claim 35, further comprising at least one additive selected from the group consisting of a filler, a pigment, a colorant, a surfactant, a sunscreen, an antioxidant, a fragrance and a preserving agent.

54. Cosmetic composition according to claim 35, wherein said composition is anhydrous.

55. Cosmetic composition according to claim 35, wherein said composition is in the form of a stick, a tube, a soft paste, with a dynamic viscosity at 25° C. of about from 1 to 40 Pa.s, a dish, an oily gel or an oily liquid.

56. A method of making up and/or caring for the skin, comprising applying a composition of claim 35, to said skin.

57. Cosmetic composition according to claim 35, the form of a lipstick, a mascara, an eyeliner, a foundation, a powder, a blusher, an eyeshadow or a body make-up.

58. Cosmetic composition according to claim 35, in the form of a moisturizing product, a deodorant or an antiperspirant.

59. A cosmetic composition according to claim 36, wherein the polyorganosiloxane contains from 2 to 30,000 organosiloxy units.

60. A cosmetic composition of claim 47, wherein the silicone oil is selected from the group consisting of a phenyltrimethicone, a phenyltrimethylsiloxy-diphenylsiloxane, a diphenylmethyldimethyltrisiloxane, a diphenyldimethicone, and a phenyldimethicone.

61. A cosmetic composition according to claim 48, wherein said oil is selected from the group consisting of isopropyl myristate, Isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate or lactate, bis(2-ethylhexyl) succinate, diisostearyl malate, glyceryl trisostearats, diglyceryl trilsostearate, stearyl alcohol, oteyl alcohol, linoleyl alcohol, linoleny alcohol, isostearyl alcohol and octyldodecanol.

62. A method of claim 56, wherein said skin is selected from the group consisting of eyelids, lips and nails.

\* \* \* \* \*